United States Patent
Kobayashi et al.

(10) Patent No.: US 12,336,850 B2
(45) Date of Patent: Jun. 24, 2025

(54) X-RAY DIAGNOSTIC APPARATUS AND TOMOSYNTHESIS IMAGING METHOD

(71) Applicant: CANON MEDICAL SYSTEMS CORPORATION, Otawara (JP)

(72) Inventors: Yoshimasa Kobayashi, Nasushiobara (JP); Yasuhiro Sugawara, Nasushiobara (JP); Seiichi Nishizuka, Nasushiobara (JP); Takehiro Fukuzaki, Utsunomiya (JP); Daisuke Sato, Utsunomiya (JP); Tatsuaki Kodaka, Nasushiobara (JP); Akitoshi Sato, Otawara (JP); Tomio Maehama, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 378 days.

(21) Appl. No.: 17/819,344

(22) Filed: Aug. 12, 2022

(65) Prior Publication Data

US 2023/0056354 A1   Feb. 23, 2023

(30) Foreign Application Priority Data

Aug. 17, 2021 (JP) ................. 2021-132521

(51) Int. Cl.
  *A61B 6/06*   (2006.01)
  *G01N 23/04*   (2018.01)
  *G01N 23/20*   (2018.01)
(52) U.S. Cl.
  CPC .............. *A61B 6/06* (2013.01); *G01N 23/04* (2013.01); *G01N 23/20* (2013.01)

(58) Field of Classification Search
  CPC ........... A61B 6/06; G01N 23/04; G01N 23/20
  See application file for complete search history.

(56) References Cited

U.S. PATENT DOCUMENTS

| | | | |
|---|---|---|---|
| 6,196,715 B1 * | 3/2001 | Nambu | A61B 6/504 378/197 |
| 9,848,840 B2 * | 12/2017 | Ohashi | A61B 6/06 |
| 2004/0109529 A1 * | 6/2004 | Eberhard | A61B 6/4028 378/23 |
| 2016/0174922 A1 | 6/2016 | Kodera et al. | |
| 2020/0319123 A1 | 10/2020 | Tanimori et al. | |

FOREIGN PATENT DOCUMENTS

| | | | |
|---|---|---|---|
| JP | 2006280517 A | * | 10/2006 |
| JP | 2010501238 A | * | 8/2007 |
| JP | 2016515877 A | * | 3/2014 |
| JP | 2015-24097 A | | 2/2015 |
| JP | 2020044265 A | * | 3/2020 |
| WO | WO 2017/209059 A1 | | 12/2017 |

* cited by examiner

*Primary Examiner* — David P Porta
*Assistant Examiner* — Fani Polyzos Boosalis
(74) *Attorney, Agent, or Firm* — Oblon, McClelland, Maier & Neustadt, L.L.P.

(57) ABSTRACT

According to one embodiment, an X-ray diagnostic apparatus includes an X-ray irradiator, a scatterer, a grid, and a detector. The X-ray irradiator irradiates X-rays. The scatterer is provided between the X-ray irradiator and an object, that scatters the irradiated X-rays. The grid is provided between the scatterer and the object, that transmits the scattered X-rays within a predetermined angular range. The detector detects X-rays transmitted through the object together with an incident angle of the X-rays.

20 Claims, 8 Drawing Sheets

X-RAY DIAGNOSTIC APPARATUS AND TOMOSYNTHESIS IMAGING METHOD

CROSS-REFERENCE TO RELATED APPLICATIONS

This application claims the benefit of priority of Japanese Patent Application No. 2021-132521, filed Aug. 17, 2021, the entire contents of which are incorporated herein by reference.

FIELD

Embodiments described herein relate generally to an X-ray diagnostic apparatus and a tomosynthesis imaging method.

BACKGROUND

Recently, some X-ray diagnostic apparatuses are capable of using tomosynthesis technology to obtain various tomographic or three-dimensional images (hereinafter called tomosynthesis image) by reconstructing multiple image data obtained by irradiating an object with X-rays from multiple discrete incident directions within a predetermined incident angle range.

One example of tomosynthesis imaging is the use of a tomosynthesis technique in which, within an incident angle range of ±15 degrees centered on the x-ray irradiation axis, the multiple image data are acquired by irradiating the object with X-rays from respective incident directions in the order of −15 degrees, −14 degrees, . . . , +15 degrees.

In tomosynthesis imaging, however, multiple X-ray images are required, which increases the time required for data collection. Therefore, the tomosynthesis image obtained by reconstruction may have strong motion artifacts. In this case, it is difficult for the user to read the image correctly.

Further, in tomosynthesis imaging, X-ray imaging is performed at each of the discrete angles. Although the collection time can be shortened by coarsening the angular increments, the tomosynthesis image obtained by reconstruction in this case is highly artifactual.

DETAILED DESCRIPTION

Hereinbelow, a description will be given of an X-ray diagnostic apparatus and a tomosynthesis imaging method according to embodiments of the present invention with reference to the drawings.

In general, according to one embodiment, an X-ray diagnostic apparatus includes an X-ray irradiator, a scatterer, a grid, and a detector. The X-ray irradiator irradiates X-rays. The scatterer is provided between the X-ray irradiator and an object, that scatters the irradiated X-rays. The grid is provided between the scatterer and the object, that transmits the scattered X-rays within a predetermined angular range. The detector detects X-rays transmitted through the object together with an incident angle of the X-rays.

Figure 1:
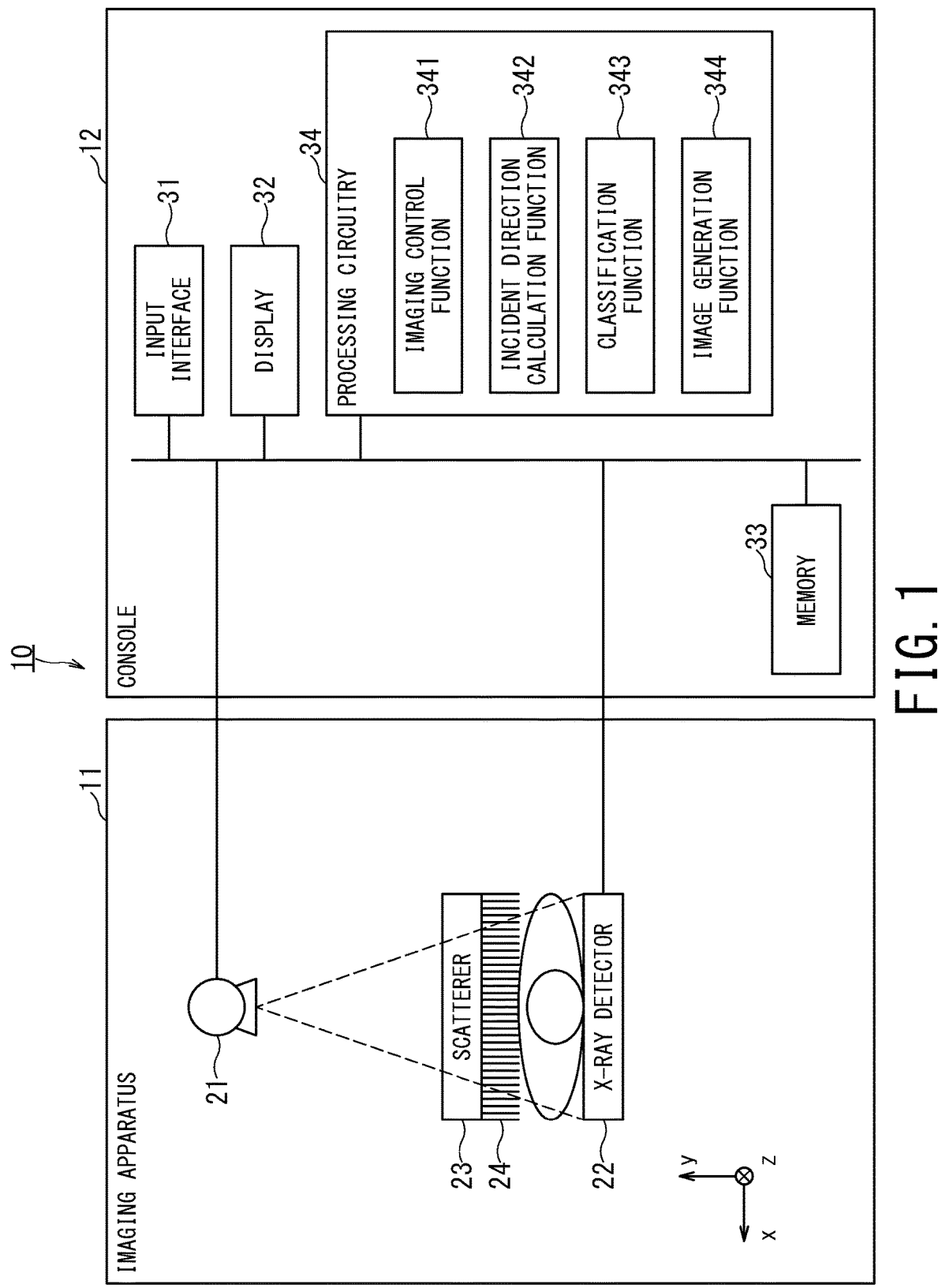
FIG. 1 is a block diagram showing a configuration of an X-ray diagnostic apparatus according to an embodiment.

FIG. 1 is a block diagram showing a configuration of an X-ray diagnostic apparatus 10 according to an embodiment. In this embodiment, the y-axis direction is parallel to the X-ray irradiation axis and normal to the scatterer, grid, and X-ray detector. In the example shown in FIG. 1, the y-axis direction parallel to the front-back direction of the object. The x-axis direction is orthogonal to the y-axis direction and parallel to the left and right directions of the object, and the z-axis direction is orthogonal to the x-axis direction and parallel to the body axis direction of the object (see FIG. 1).

The X-ray diagnostic apparatus 10 has an imaging apparatus 11 and a console 12. The imaging apparatus 11 and the console 12 may be constructed as a single unit, or a part of the console 12 may be constructed as a separate unit.

The imaging apparatus 11 consists of an X-ray irradiator 21, an X-ray detector 22, a scatterer 23, and a grid 24.

The X-ray irradiator 21 is positioned opposite the X-ray detector 22 across the object and irradiates the object with X-rays. The X-ray irradiator 21 and X-ray detector 22 may be supported at respective ends of a support member, such as an arm, for example. When the X-ray diagnostic apparatus 10 is a mammography apparatus, for example, the X-ray irradiator 21 is provided at the upper end of an arm which lower end is supported by an imaging table that holds the X-ray detector 22 inside.

The X-ray irradiator 21 has an X-ray tube and an X-ray diaphragm. The X-ray tube is a vacuum tube that irradiates thermal electrons from a cathode (filament) to an anode (target) by applying a high voltage supplied from a high-voltage power supply. The X-ray diaphragm is, for example, an X-ray variable diaphragm including multiple lead blades, for example.

The X-ray detector 22 detects the incident direction of incident X-rays that are scattered by the scatterer 23 and then transmitted through the object.

For example, an electron track detection device using Compton scattering can be used as the X-ray detector 22 that can detect the incident direction of the X-rays. The details of the configuration and operation of the X-ray detector 22 are described below using FIG. 2.

The scatter 23 is provided between the X-ray irradiator 21 and the object, and scatters the X-rays irradiated from the X-ray irradiator 21. The scatterer 23 is composed of a material capable of scattering X-rays and is made of, for example, PMMA or water.

The grid 24 is provided between the scatterer 23 and the object, and has a plurality of holes through which X-rays are transmitted, and the holes limit the incident angle of the X-rays scattered by the scatterer 23 with respect to the object within the predetermined angular range.

Specifically, the grid 24 is a collimator of the parallel-porous type made of a metal with a high X-ray attenuation coefficient and a high X-ray shielding capacity, such as lead or tungsten, with many holes that transmit X-rays. When X-rays irradiated from the X-ray irradiator 21 irradiate the metal of the grid 24, a photoelectric effect occurs and the X-rays are annihilated. Only the X-rays that pass through the small holes in grid 24 reach the X-ray detector 22 via the object, and lead to the detection of photons. The predetermined incident angle (e.g., ±15 degrees) limited by grid 24 and the spatial resolution of the grid 24 vary depending on the type of grid 24. The type of grid 24 depends on the aperture shape of the holes, the arrangement of the holes, the thickness of the septum, and the like. The holes in the grid 24 are provided to be perpendicular to the scatterer 23 and the X-ray detector 22 (see FIG. 1).

The grid 24 may be removably provided on the object side of the scatterer 23. In this case, the grid 24 can be easily replaced, and the type of the grid 24 that meets the purpose of the inspection can be used quickly and appropriately. The details of the configuration and operation of the grid 24 are described below using FIGS. 3-6. The X-ray diagnostic system 10 may not be provided with the grid 24.

Meanwhile, the console 12 has an input interface 31, a display 32, a memory 33, and processing circuitry 34.

The input interface 31 may include common pointing devices such as joysticks, trackballs, trackball mice, keyboards, touch panels, and numeric keypads, and hand switches for indicating the timing of X-ray irradiation, which outputs operation input signals corresponding to user operations to the processing circuitry 34. The input interface 31 accepts instructions to turn on or off X-ray imaging as well as the setting of X-ray imaging conditions, including the classification width of X-ray detection data (angle width of incidence, e.g., every 0.5 degrees) in tomosynthesis image generation according to the embodiment. Some or all of the functions of the input interface 31 may be provided in the imaging apparatus 11.

Display 32 consists of a general display output device such as a liquid crystal display or an OLED (Organic Light Emitting Diode) display, and displays various information according to the control of the processing circuitry 34.

The memory 33 includes recording media, such as magnetic or optical recording media or semiconductor memory, that can be read by the processor, and some or all of the programs and data stored in these recording media may be downloaded via a network.

The processing circuitry 34 realizes the function of overall control of the X-ray diagnostic apparatus 10. The processing circuitry 34 is a processor that performs processing to reduce artifacts in tomosynthesis images by reading out and executing the tomosynthesis image generation program stored in memory 33.

As shown in FIG. 1, the processor of the processing circuitry 34 realizes an imaging control function 341, an incident direction calculation function 342, a classification function 343, and an image generation function 344. Each of these functions is stored in memory 33 in the form of a program.

The imaging control function 341 controls the imaging apparatus 11 according to the imaging protocol selected by the user via input interface 31, for example, to control the X-ray imaging of the object. The imaging protocol defines a series of procedures for collecting the desired image data, and includes information on the imaging site, as well as X-ray imaging condition such as the tube current and the tube voltage applied to the X-ray irradiator 21, and the setting of the angle width of incidence for the tomosynthesis image generation according to the embodiment.

The incident direction calculation function 342 calculates the incident direction (incident angle) of the X-rays based on the X-ray detection data output by the X-ray detector 22. The incident direction calculation function 342 and the X-ray detector 22 constitute the detector (detector unit). The detector unit detects the X-rays transmitted through the object together with the incident angle of the X-rays. The incident direction calculation function 342 may be provided in the X-ray detector 22. In this case, the X-ray detector 22 may have a processor that implements the incident direction calculation function 342.

The classification function 343 classifies the X-ray detection data of each X-ray photon incident at an incident angle limited by the multiple holes in the grid 24 by a predetermined angle width of incidence.

The image generation function 344 generates a tomosynthesis image of the object based on the image signal corresponding to the intensity of the X-rays and the incident angle of the X-rays detected by the detector unit. Specifically, the image generation function 344 generates the tomosynthesis image of the object based on the X-ray detection data classified by the predetermined angle width of incidence. The image generation function 344 reconstructs a tomosynthesis image from the classified X-ray detection data using, for example, a filtered back projection (FBP) method or an iterative reconstruction (IR) method. The incident angle information of the classified X-ray detection data is used for back projection and inverse projection in the reconstruction process.

The tomosynthesis imaging method performed by the X-ray diagnostic apparatus 10 according to the embodiment will now be described.

Generally, in X-ray imaging for generating tomosynthesis images, while changing the positions of the X-ray source and the X-ray detection unit within a predetermined incident angle range (e.g., ±15 degrees), the X-ray irradiation to the object is performed at discrete angles (e.g., 1 degree) from different incident angles.

However, in this type of tomosynthesis imaging, the collection time is long because multiple X-ray imaging is required. For this reason, the state of the object may change between the first X-ray irradiation (in the above example, irradiation at −15 degrees) and the last X-ray irradiation (in the above example, irradiation at +15 degrees), due to the body movement of the object, or due to changes in the density of the contrast agent in the area to be observed. In this case, the tomosynthesis image obtained by reconstruction becomes an image containing strong motion artifacts, making it difficult for the user to read the image correctly.

Further, in this type of tomosynthesis imaging, X-ray imaging is performed at each of the discrete angles. When the angular increments are made coarse (e.g., every 3 degrees instead of every 1 degree in the above example), the acquisition time can be shortened, but the tomosynthesis image obtained by reconstruction is highly artifactual. On the other hand, when the angular increments are made finer (e.g., every 0.5 or 0.25 degrees instead of every 1 degree in the above example), the acquisition time becomes longer. One possible measure to shorten the collection time for finer angular increments is to increase the frame rate of X-ray imaging (e.g., from 15 fps to 30 fps). However, in consideration of the performance limit of each component, such as the X-ray detector 22, it is not practical to increase the frame rate. Accordingly, finer angular increments inevitably increase the collection time, and the tomosynthesis image obtained by reconstruction is still an image containing strong motion artifacts.

In the X-ray diagnostic apparatus 10 according to the present embodiment, the x-ray irradiator 21 irradiates X-rays toward the object without changing its position relative to the object and the x-ray detector 22, and without moving from one single position directly opposite the X-ray detector 22. X-rays irradiated from the X-ray irradiator 21 are scattered by the scatterer 23, directed toward the object at various incident angles, and directed toward the x-ray detector 22 after passing through the object. Then, an incident angle is associated with each corresponding X-ray photon incident on the X-ray detector 22 by the X-ray detector 22 and the incident direction calculation function 342. In the case of using the grid 24, the X-rays scattered by scatterer 23 are limited by the grid 24 to X-rays whose incident angle fall within a predetermined incident angle range (e.g., within ±15 degrees).

Therefore, without moving the X-ray source to change the X-ray incident direction, the X-ray irradiator 21 can irradiate X-rays from a single position to irradiate photons to the object within a predetermined incident angle range and obtain X-ray detection data for each desired angle width of incidence. Therefore, tomosynthesis images with fine angular increments can be easily generated in a very short time.

For this reason, the X-ray diagnostic apparatus 10 according to this embodiment has the X-ray detector 22 capable of detecting the incident direction (incident angle) of the X-ray and the grid 24 that limits the incident direction of the X-ray such that only photons within the predetermined incident angle are irradiated onto the object.

Next, the configuration and operation of the X-ray detector 22 are described with reference to FIG. 2.

Figure 2:
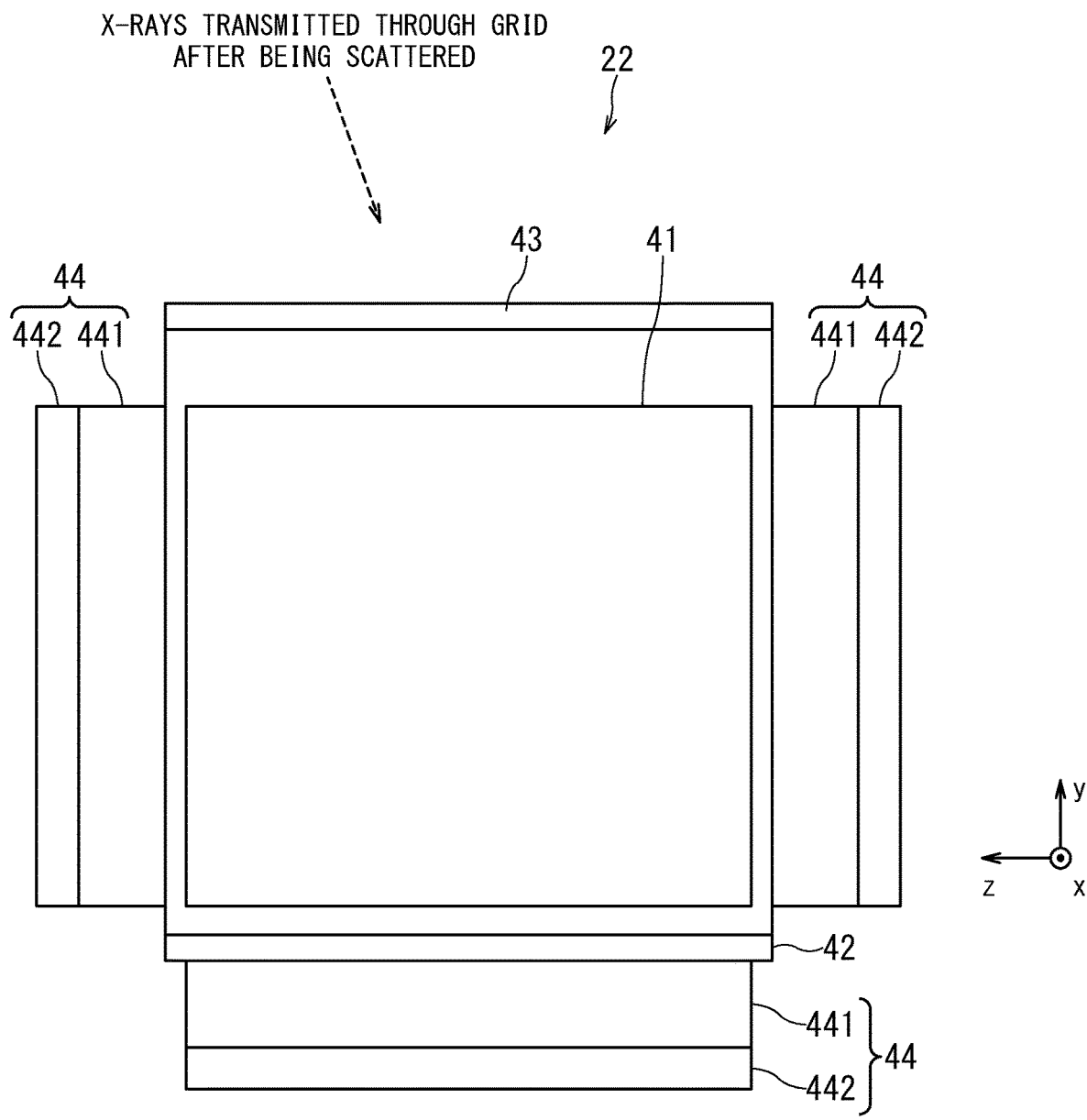
FIG. 2 is a cross-sectional view of an X-ray detector.

FIG. 2 is a cross-sectional view of the X-ray detector 22. FIG. 2 shows the yz-section of the X-ray detector 22.

The X-ray detector 22 according to this embodiment has a configuration that can detect the incident direction (incident angle) of the X-rays. FIG. 2 shows an example of the X-ray detector 22 when the X-ray detector 22 and the incident direction calculation function 342 constitutes an electron tracking type detector using Compton scattering. Detectors such as an electron-tracking Compton camera (ETCC) are known as electron-tracking type detector.

The X-ray detector 22 has a chamber 41 in the center thereof that has a rectangular shape and is filled with gas inside. The gas inside the chamber 41 is, for example, argon at 1 to several atmospheres.

The X-rays within the predetermined incident angle, that are scattered by the scatterer 23 and transmitted through the grid 24, are incident into the chamber 41 from above in the y-axis direction. A part of the incident X-rays interact with electrons of gas atoms in chamber 41, resulting in Compton scattering. The Compton scattering changes the direction of the incident X-rays, and the incident X-rays become scattered X-rays. The X-ray corresponding to one Compton scattering is one photon. The electrons that receive energy from the incident X-rays are ejected from the gas atoms as recoiling electrons.

A two-dimensional gas amplification position detector 42 is provided at the bottom of the chamber 41. For example, a μ PIC (Micro Pixel Chamber) can be used as the two-dimensional gas amplified position detector 42. The two-dimensional gas amplification position detector 42 according to the embodiment is a type of micro pattern gas detector (MPGD), which acquires the incident position of the charged particles. A drift plane 43 is placed above the chamber 41.

In the chamber 41, an electric field is formed from the two-dimensional gas amplification position detector 42 to the drift plane 43. The recoiling electrons ionize electrons from the gas atoms in the chamber 41 to form electron clouds. The electron clouds are guided by the electric field to the two-dimensional gas amplification position detector 42 and is detected by the two-dimensional gas amplification position detector 42.

Outside each of the four sides of the chamber 41 and the underside of the two-dimensional gas amplification position detector 42, a scattering X-ray detector 44 is provided. The scattering X-ray detector 44 includes a scintillator array 441, in which scintillators are arranged in two dimensions, and a detection circuit 442 using a photomultiplier tube or similar device that detects fluorescence from each scintillator. The scintillator array 441 is located between the chamber 41 and the detection circuit 442. When the scattered X-rays from chamber 41 are absorbed by one of the scintillators, the detection circuit 442 detects the light emitted from the scintillators, whereby the detection position of the scattered X-rays is acquired.

The scattering X-ray detector 44 may be located only at the bottom of the chamber 41. The four scattering X-ray detectors 44 on the sides are useful for improving detection efficiency.

When the scattered X-rays enter one of the five scattering X-ray detectors 44 (see FIG. 2), the scattering X-ray detector 44 acquires the detection position and detection time.

On the other hand, the recoiling electrons proceed while losing energy as they ionize electrons of the gas atoms in the chamber 41. The electron clouds of ionized electrons move toward the two-dimensional gas amplification position detector 42 due to the electric field formed in the chamber 41. The two-dimensional gas amplification position detector 42 has micro-detector elements arranged in two dimensions. Each micro-detector element detects incoming ionized electrons, whereby the detection position and detection time of the ionized electrons are acquired. The two-dimensional gas amplification position detector 42 is an example of an electron detector.

The detection information on the scattered X-rays and the ionized electrons is given to the incident direction calculation function 342 of the processing circuitry 34.

The incident direction calculation function 342 is a function that calculates the incident direction (incident angle) of the incident X-ray on the X-ray detector 22 using the Compton scattering formula based on these X-ray detection data (detection information on the scattered X-rays and the ionized electrons), which are the detection results of the X-ray detector 22.

The incident direction calculation function 342 may determine the energy of the incident X-rays based on the law of conservation of energy, that is, based on the fact that the sum of the energy of the scattered X-rays and the energy of the recoiling electrons is equal to the sum of the energy of the incident X-rays and the energy of electrons that can be regarded as stationary. In this case, the incident direction calculation function 342 can exclude, among X-rays incident into the chamber 41 of the X-ray detector 22, whose energy is smaller than a predetermined value from being used for generating image.

The configuration and operation of the grid 24 are now described using FIGS. 3-6.

Figure 3:
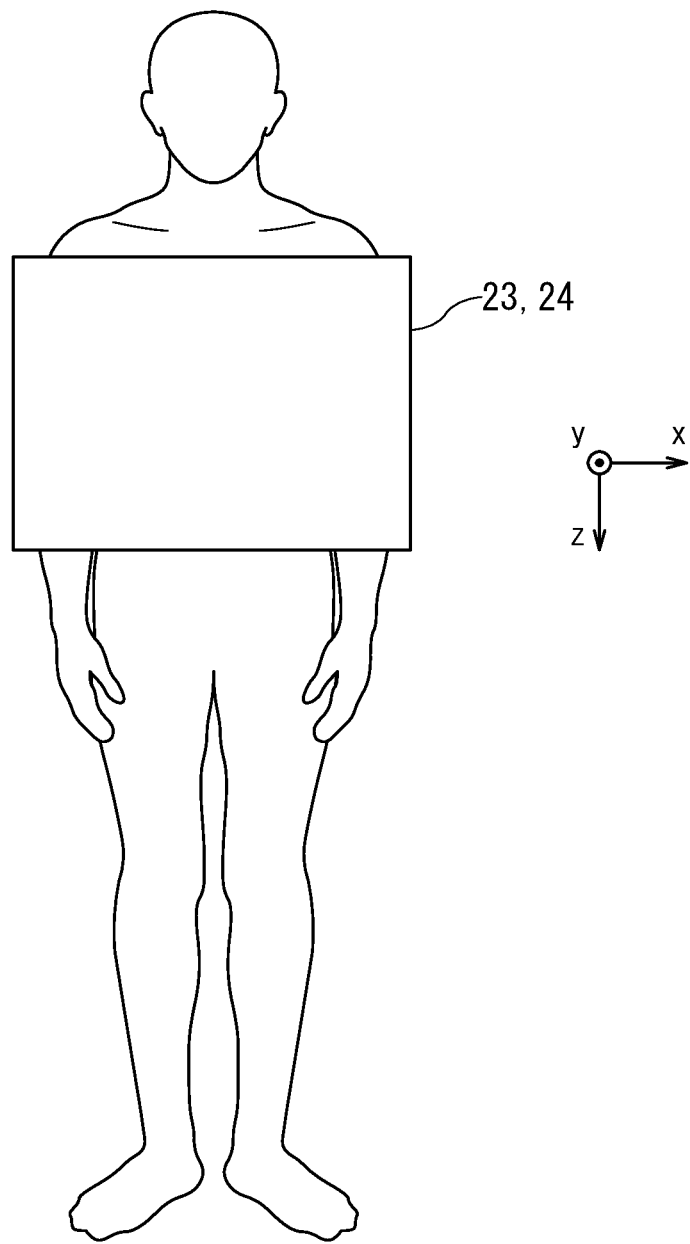
FIG. 3 is an illustration showing an example of the positional relationship between a scatterer, grid, and object as seen from an X-ray irradiator.

FIG. 3 is an illustration showing an example of the positional relationship between the scatterer 23, the grid 24, and the object as seen from the X-ray irradiator 21. FIG. 3 shows an example when the area to be observed is the lung field.

Figure 4A:
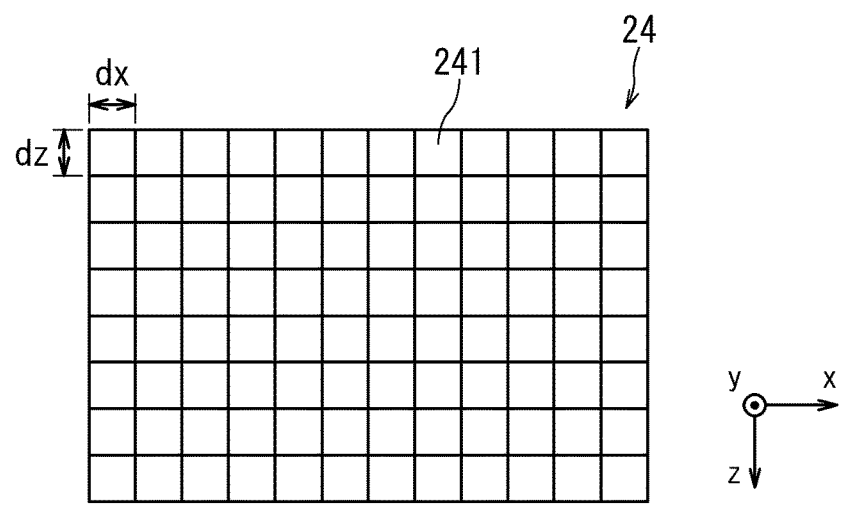
FIG. 4A is an xz cross-sectional view showing an example of a configuration of the grid when the aperture shape of each of multiple holes in the grid is square.
Figure 4B:
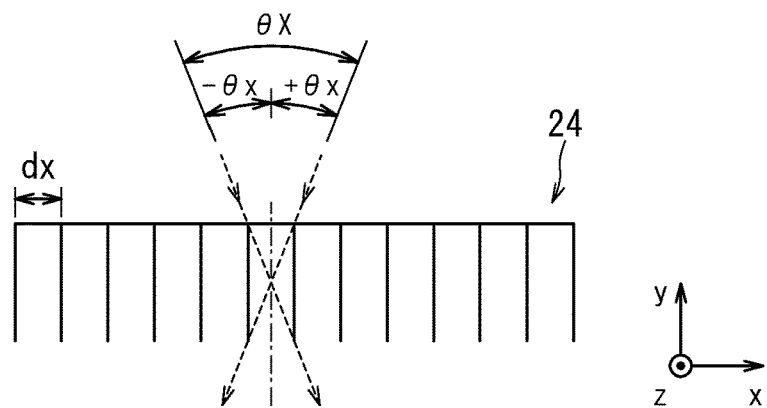
FIG. 4B is an xy cross-sectional view showing an example of a configuration of the grid when the aperture shape of each of the multiple holes in the grid is square.

FIG. 4A is an xz cross-sectional view showing an example of a configuration of the grid 24 when the aperture shape of each of multiple holes 241 in the grid 24 is square. FIG. 4B shows an xy cross-sectional view, and FIG. 4C shows a yz cross-sectional view.

Figure 4C:
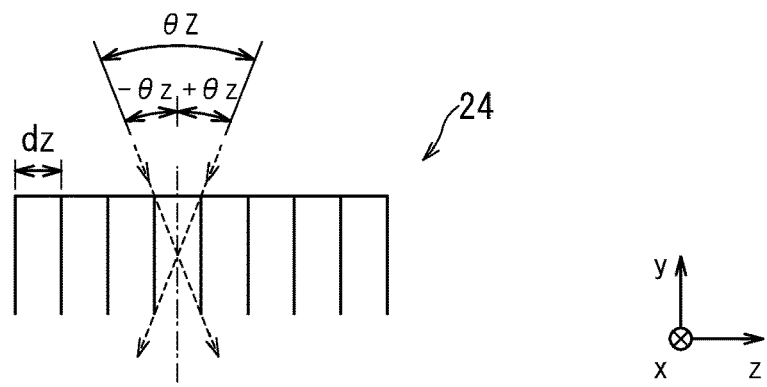
FIG. 4C is a yz cross-sectional view showing an example of a configuration of the grid when the aperture shape of each of the multiple holes in the grid is square.

In FIG. 4A-4C, an example is shown in which the opening of each hole 241 in the grid 24 has an edge of length dx in the x-direction, an edge of length dz in the z-direction, and the lengths of dx and dz are identical.

In this case, the incident angle ±θx (e.g., ±15 degrees) in the x-direction and its angle width θX (e.g., 30 degrees) in the x-direction limited by the grid 24 (see FIG. 4B) is equal to the incident angle ±θz in the z-direction and its angular width θZ (see FIG. 4C) in the z-direction.

The classification function 343 classifies the X-ray detection data of the X-ray photons incident at the incident angle limited by the multiple holes 241 of the grid 24 by each predetermined angle width of incidence.

At this time, unlike general tomosynthesis imaging in which X-ray imaging is repeated while changing the position of the X-ray source in predetermined incident angle increments (for example, every 1 degree), the X-ray detection data according to this embodiment can be classified by any angular increments.

Then, the image generation function 344 generates a tomosynthesis image of the object based on the X-ray detection data classified by the classification function 343 (e.g., every 0.25 degree), and displays the tomosynthesis image on the display 32.

With the X-ray diagnostic apparatus 10 according to this embodiment, the X-ray irradiator 21 can almost simultaneously irradiate X-rays toward the object within the incident angle limited by the grid 24, without changing its position relative to the object and the X-ray detector 22 or moving from a single position. Therefore, X-ray detection data can be collected in a very short time. Hence, according to the X-ray diagnostic apparatus 10, a high-quality tomosynthesis image containing very few motion artifacts can be generated.

Further, since the X-ray diagnostic apparatus 10 can easily acquire X-ray detection data classified by any desired angular increments, artifacts associated with coarse angular increments in the tomosynthesis image can be significantly reduced.

Moreover, the X-ray diagnostic apparatus 10 according to this embodiment can acquire X-ray detection data of incident angle ±θx in the x-direction and X-ray detection data of incident angle ±θz in the z-direction almost simultaneously in a very short time by simply irradiating the X-rays from a single position. In addition, for each of the x- and z-directions, the angular increments for classifying the X-ray detection data can be freely set.

Figure 5A:
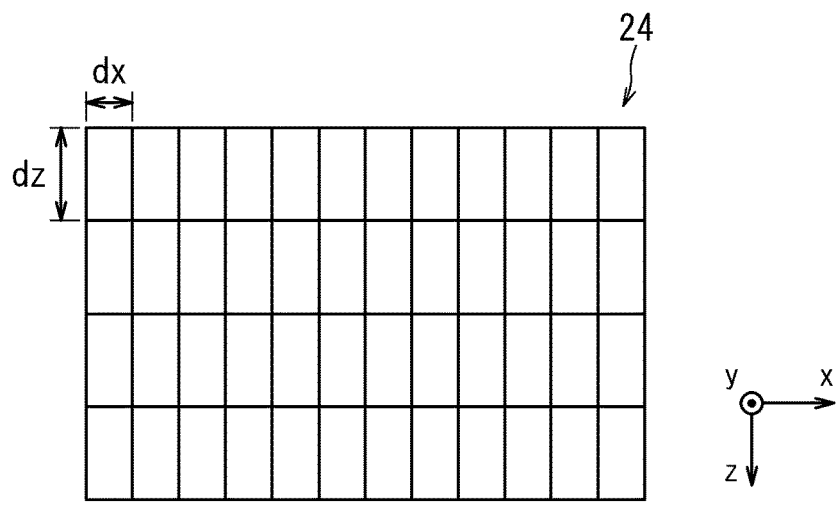
FIG. 5A is an xz cross-sectional view showing an example of a configuration of the grid when the aperture shape of each of the multiple holes in the grid is rectangular.
Figure 5B:
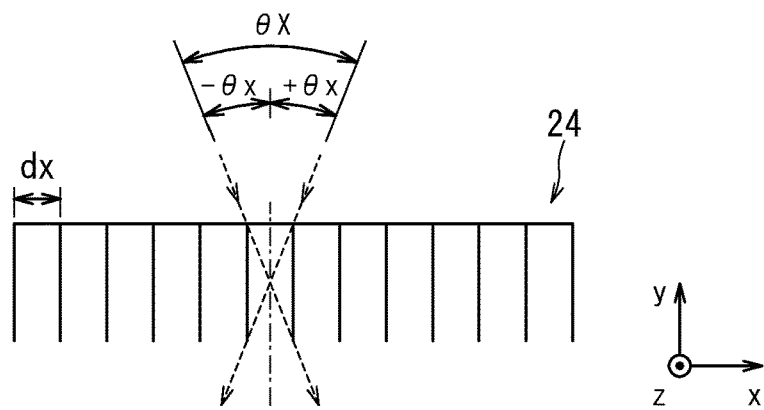
FIG. 5B is an xy cross-sectional view showing an example of a configuration of the grid when the aperture shape of each of the multiple holes in the grid is rectangular.

FIG. 5A is an xz cross-sectional view showing an example of a configuration of the grid 24 when the aperture shape of each of the multiple holes 241 in the grid 24 is rectangular. FIG. 5B is an xz cross-sectional view, and FIG. 5C is a yz cross-sectional view.

Figure 5C:
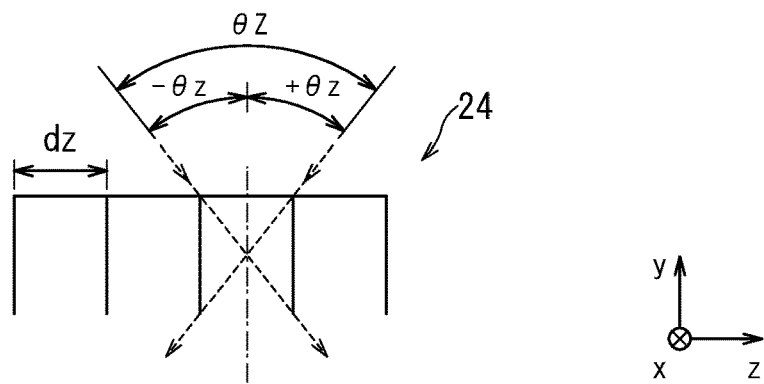
FIG. 5C is a yz cross-sectional view showing an example of a configuration of the grid when the aperture shape of each of the multiple holes in the grid is rectangular.

In FIG. 5A-5C, an example is shown in which the opening of each hole 241 of the grid 24 has an edge of length dx in the x-direction and an edge of length dz in the z-direction, and the length dz is longer than dx.

When observing a lesion in the lung field, the ribs may interfere with the visibility of the lesion. The ribs extend in the left and right directions of the object.

In this case, it is preferable to use the grid 24 having a long opening in the body axis direction (z-direction), as shown in FIG. 5A-5C.

By using the grid 24 with an aperture longer in the body axis direction (z-direction) than in the left-right direction (x-direction), it is possible to blur the body axis direction of the object in the tomosynthesis image, which is generated from X-ray detection data of incident angle ±θz (e.g., ±30 degrees) in the body axis direction. Therefore, in the tomosynthesis image, the visibility of the ribs can be reduced and the lesion can be easily observed.

Figure 6:
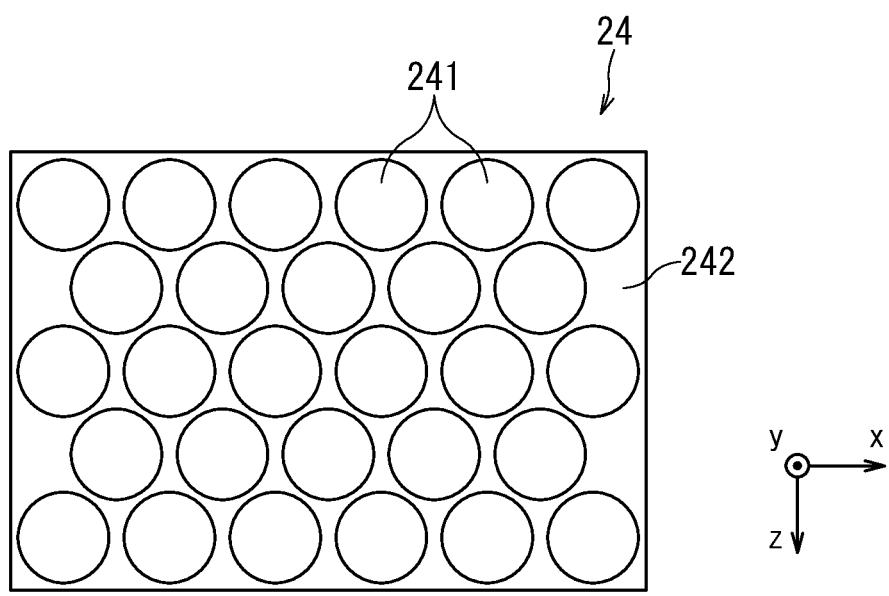
FIG. 6 is an xz cross-sectional view showing an example of a configuration of the grid when the aperture shape of each of the multiple holes in the grid is circular.

FIG. 6 is an xz cross-sectional view showing an example of a configuration of the grid 24 when the aperture shape of each of the multiple holes 241 in the grid 24 is circular.

When observing sinuses or orbitals, bones are present in multiple directions rather than in a specific direction in the field of view. In this case, it is preferred to perform X-ray imaging by using the grid 24 having a circular or elliptical aperture shape. In this case, it is possible to collect X-ray detection data equivalent to the case where X-ray imaging is performed by moving the X-ray source along a circular path in general tomosynthesis imaging.

By changing the aperture shape of the hole 241 in the grid 24, the X-ray irradiator 21 can easily imitate the X-ray source moving in linear, circular, and elliptical orbits in general tomosynthesis imaging by simply irradiating X-rays from a single position.

Next, an example of the operation of the X-ray diagnostic apparatus 10 and the tomosynthesis imaging method will be described.

Figure 7:
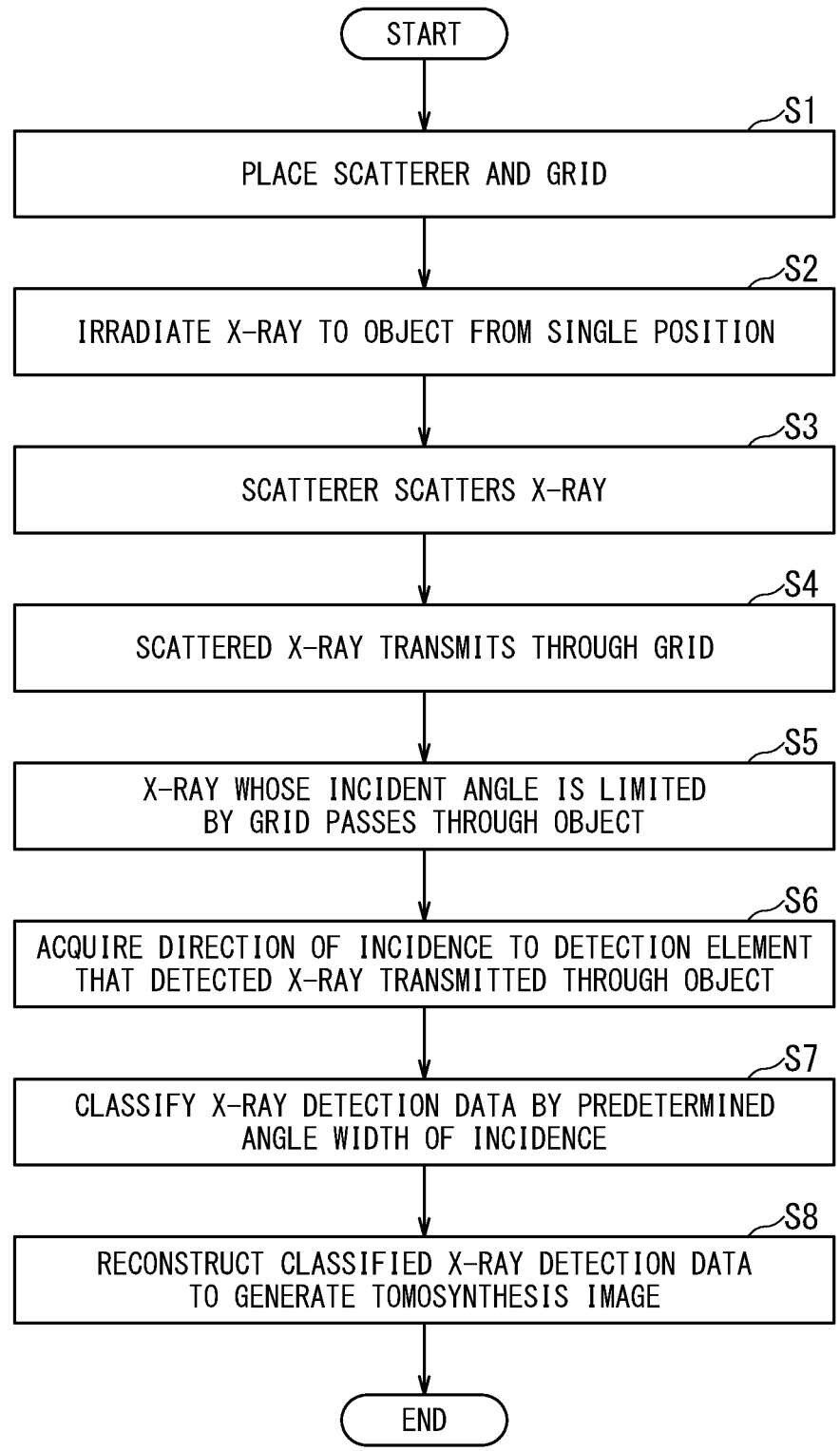
FIG. 7 is a flowchart showing an example of a procedure for reducing artifacts in a tomosynthesis image using the X-ray diagnostic apparatus shown in FIG. 1.

FIG. 7 is a flowchart showing an example of a procedure for reducing artifacts in the tomosynthesis image using the X-ray diagnostic apparatus 10 shown in FIG. 1. In FIG. 7, reference numerals with numbers attached to S indicates each step of the flowchart.

This procedure starts when the X-ray irradiator 21 and the X-ray detector 22 are positioned opposite to each other with the object in between and the X-ray irradiator 21 faces the object and the X-ray detector 22.

First, in step S1, the scatterer 23 and the grid 24 are placed at the X-ray irradiator 21 side of the object, in the order of the scatterer 23 and the grid 24 from the X-ray irradiator 21 side. The scatter 23 and the grid 24 is preferably adjacent to each other. Also, the grid 24 and the object are preferably in close proximity, and more preferably in close contact (see FIG. 1).

Next, in step S2, the X-ray irradiator 21 irradiates X-rays toward the object from a single position.

The X-rays irradiated from the X-ray irradiator 21 toward the object are scattered by the scatterer 23 (step S3), and only the X-rays within the incident angle limited according to the aperture shape of the holes 241 in the grid 24 are transmitted through the grid 24 (step S4), and then pass through the object toward the X-ray detector 22 (step S5).

Next, in step S5, for each photon of X-rays incident on the chamber 41, the X-ray detector 22 detects and outputs the detection position and detection time of the scattered X-rays due to Compton scattering, as well as the detection position and detection time of the ionized electrons based on recoiling electrons due to Compton scattering. The incident direction calculation function 342 calculates the incident direction of the X-rays incident into the chamber 41 for each photon based on these X-ray detection data.

Next, in step S6, the classification function 343 classifies the X-ray detection data based on the X-ray photons incident at the incident angles limited by the plurality of holes 241 in the grid 24 by the predetermined angle width of incidence.

Then, in step S7, the image generation function 344 reconstructs the X-ray detection data classified by the predetermined incident angle width to generate tomosynthesis images of the object.

The calibration image data reconstructed based on the X-ray detection data of the ambient gas may be stored in the memory 33 without placing the object in advance. In this case, the image generation function 344 may calibrate the tomosynthesis image of the object with the calibration image data, that is, so-called air calibration may be performed.

In the above manner, it is possible to generate the tomosynthesis image based on the X-ray detection data with fine angular increments by having the X-ray irradiator 21 irradiate X-rays from a single position, whereby the artifacts in the tomosynthesis image are significantly reduced.

With the X-ray diagnostic apparatus 10 according to this embodiment, the tomosynthesis image based on the X-ray detection data with fine angular increments can be generated by irradiating X-rays from a single position toward the object without moving the X-ray irradiator 21. Therefore, the required amount of X-ray detection data can be collected in a very short time, and a high-quality tomosynthesis image containing extremely few motion artifacts can be generated. Further, artifacts caused by the roughness of angular increments in the tomosynthesis image can be significantly reduced.

Still further, the X-ray diagnostic apparatus 10 according to this embodiment does not require the X-ray irradiator 21 and the X-ray detector 22 to be moved during tomosynthesis imaging. This prevents the risk of interference between the X-ray irradiator 21 or the X-ray detector 22 and the object or other equipment such as injectors provided around the X-ray diagnostic apparatus 10. Hence, according to the X-ray diagnostic apparatus 10, tomosynthesis imaging can be performed very safely.

Figure 8:
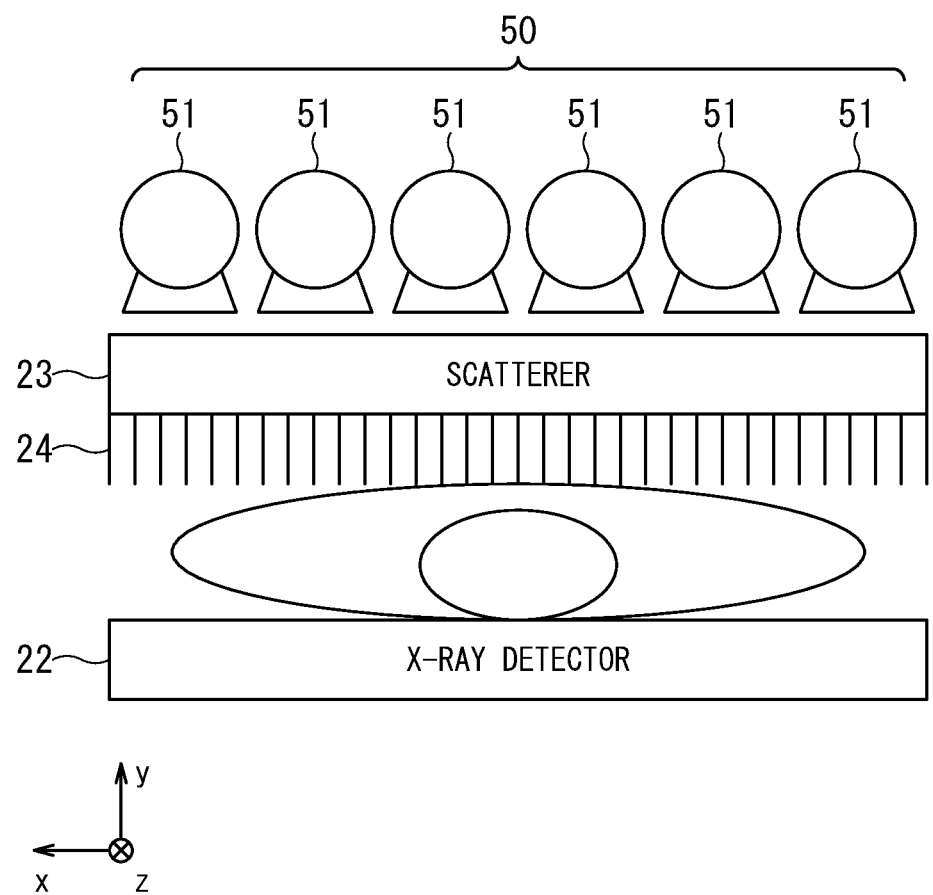
FIG. 8 is an illustration of a modification of the X-ray irradiator.

FIG. 8 is an illustration of a modification of the X-ray irradiator 21. As shown in FIG. 8, the X-ray diagnostic apparatus 10 may have an X-ray irradiator group 50 including a plurality of small X-ray irradiators 51 arranged on a plane perpendicular to the X-ray irradiation axis. Such configuration can significantly shorten the distance between the X-ray irradiator 51 and the X-ray detector 22 (the distance between the focal point of the X-ray tube and the X-ray detector surface (SID: Source Image Receptor Distance)) that allows X-ray irradiation on the entire area to be observed in the object. Therefore, the X-ray diagnostic apparatus 10 can be downsized, and can be installed in a small room or in a medical examination car. Further, since the aperture of each of the X-ray irradiators 51 can be narrowed to reduce the viewing angle, an image distortion at the periphery of the X-ray irradiation area can be reduced.

According to at least one of the above-described embodiments, artifacts in the tomosynthesis image can be reduced.

In the above-described embodiments, the term "processor" means, for example, a circuit such as a special-purpose or general-purpose CPU (Central Processing Unit), a special-purpose or general-purpose GPU (Graphics Processing Unit), an ASIC, and a programmable logic device including: an SPLD (Simple Programmable Logic Device); a CPLD (Complex Programmable Logic Device); and an FPGA. When the processor is, for example, a CPU, the processor implements various functions by reading out programs stored in a memory and executing the programs.

Additionally, when the processor is, for example, an ASIC, instead of storing the programs in the memory, the functions corresponding to the respective programs are directly incorporated as a logic circuit in the circuit of the processor. In this case, the processor implements various functions by hardware processing in which the programs incorporated in the circuit are read out and executed. Further, the processor can also implement various functions by executing software processing and hardware processing in combination.

Although a description has been given of the case where a single processor of the processing circuitry implements each function in the above-described embodiments, the processing circuitry may be configured by combining a plurality of independent processors which implement the respective functions. When a plurality of processors are provided, the memory for storing the programs may be individually provided for each processor or one memory may collectively store the programs corresponding to the functions of all the processors.

While certain embodiments have been described, these embodiments have been presented by way of example only, and are not intended to limit the scope of the inventions. These embodiments can be implemented in various other aspects, and various omissions, substitutions, changes, and combinations of embodiments can be made without departing from the spirit of the invention. These embodiments and modifications thereof are included in the scope of the invention and the gist thereof, and are also included in the invention described in the claims and the equivalent scope thereof.

The invention claimed is:

1. An X-ray diagnostic apparatus, comprising:
   an X-ray irradiator irradiating X-rays;
   a scatterer, provided between the X-ray irradiator and an object, that scatters the irradiated X-rays;
   a grid, provided between the scatterer and the object, that transmits the scattered X-rays within a predetermined angular range; and
   a detector detecting X-rays transmitted through the object together with an incident angle of the X-rays.

2. The X-ray diagnostic apparatus according to claim 1, further comprising processing circuitry configured to generate a tomosynthesis image of the object based on an image signal corresponding to an intensity and the incident angle of the X-rays detected by the detector.

3. The X-ray diagnostic apparatus according to claim 2, wherein the grid is placed between the scatterer and the object and has a plurality of holes through which X-rays are transmitted, and
   the holes limit the incident angle of the X-rays scattered by the scatterer with respect to the object within the predetermined angular range.

4. The X-ray diagnostic apparatus according to claim 3, wherein an aperture shape of each of the plurality of holes in the grid is square.

5. The X-ray diagnostic apparatus according to claim 3, wherein an aperture shape of each of the plurality of holes of the grid is rectangle where a length of sides along a body axis direction of the object and a length of sides perpendicular to the body axis direction are different.

6. The X-ray diagnostic apparatus according to claim 3, wherein an aperture shape of each of the plurality of holes of the grid is circular or elliptical.

7. The X-ray diagnostic apparatus according to claim 3, wherein the X-ray irradiator irradiates the X-rays toward the object without moving from a single position, and the processing circuitry is further configured to:
classify X-ray detection data for each incident X-ray photon limited to the predetermined angular range by the plurality of holes in the grid, by a predetermined angle width of incidence within the predetermined angular range; and
generate the tomosynthesis image of the object based on the X-ray detection data classified by the predetermined angle width of incidence.

8. The X-ray diagnostic apparatus according to claim 3, wherein the detector is a detector utilizing Compton scattering, and
the apparatus further comprises:
a chamber;
a scattering X-ray detector detecting a detection position and a detection time of scattered X-rays due to Compton scattering of the X-rays that are scattered by the scatterer, transmitted through the object, and enter the chamber; and
an electron detector detecting a detection position and a detection time of ionized electrons based on recoiling electrons due to the Compton scattering; and
the processing circuitry is further configured to determine the incident angle of the X-rays based on detection results of the scattering X-ray detector and the electron detector.

9. The X-ray diagnostic apparatus according to claim 3, further comprising a memory storing a calibration image based on X-ray detection data according to X-rays that are transmitted through an ambient gas instead of the object and detected by the detector, and
the processing circuitry is further configured to calibrate the tomosynthesis image of the object with the stored calibration image to obtain a calibrated tomosynthesis image.

10. The X-ray diagnostic apparatus according to claim 2, wherein the X-ray irradiator irradiates the X-rays toward the object without moving from a single position, and the processing circuitry is further configured to:
classify X-ray detection data for each incident X-ray photon limited to the predetermined angular range by the plurality of holes in the grid, by a predetermined angle width of incidence within the predetermined angular range; and
generate the tomosynthesis image of the object based on the X-ray detection data classified by the predetermined angle width of incidence.

11. The X-ray diagnostic apparatus according to claim 2, wherein the detector is a detector utilizing Compton scattering,
the apparatus further comprises:
a chamber;
a scattering X-ray detector detecting a detection position and a detection time of scattered X-rays due to Compton scattering of the X-rays that are scattered by the scatterer, transmitted through the object, and enter the chamber; and
an electron detector detecting a detection position and a detection time of ionized electrons based on recoiling electrons due to the Compton scattering; and
the processing circuitry is further configured to determine the incident angle of the X-rays based on detection results of the scattering X-ray detector and the electron detector.

12. The X-ray diagnostic apparatus according to claim 2, further comprising a memory storing a calibration image based on X-ray detection data according to X-rays that are transmitted through an ambient gas instead of the object and detected by the detector, and
the processing circuitry is further configured to calibrate the tomosynthesis image of the object with the stored calibration image to obtain a calibrated tomosynthesis image.

13. The X-ray diagnostic apparatus according to claim 1, wherein the X-ray irradiator irradiates the X-rays toward the object without moving from a single position, and
wherein the apparatus further comprises processing circuitry configured to:
classify X-ray detection data for each incident X-ray photon limited to the predetermined angular range by the plurality of holes in the grid, by a predetermined angle width of incidence within the predetermined angular range; and
generate a tomosynthesis image of the object based on the X-ray detection data classified by the predetermined angle width of incidence.

14. The X-ray diagnostic apparatus according to claim 1, wherein the detector is a detector utilizing Compton scattering, and
the apparatus further comprises;
a chamber;
a scattering X-ray detector detecting a detection position and a detection time of scattered X-rays due to Compton scattering of the X-rays that are scattered by the scatterer, transmitted through the object, and enter the chamber;
an electron detector detecting a detection position and a detection time of ionized electrons based on recoiling electrons due to the Compton scattering; and
processing circuitry configured to determine the incident angle of the X-rays based on detection results of the scattering X-ray detector and the electron detector.

15. The X-ray diagnostic apparatus according to claim 1, wherein:
the X-ray irradiator includes a plurality of X-ray irradiators irradiating X-rays; and
the X-ray irradiators are arranged on a plane perpendicular to the X-ray irradiation axis.

16. A tomosynthesis imaging method comprising:
irradiating X-rays using an X-ray irradiator;
scattering the irradiated X-rays using a scatterer provided between the X-ray irradiator and an object;
transmitting the scattered X-rays within a predetermined angular range through a grid provided between the scatterer and the object; and
detecting X-rays transmitted through the object together with an incident angle of the X-rays.

17. The tomosynthesis imaging method according to claim 16, further comprising
generating a tomosynthesis image of the object based on an image signal corresponding to an intensity and the incident angle of the X-rays detected by the detector.

18. The tomosynthesis imaging method according to claim 17, wherein the step of transmitting the scattered X-rays within a predetermined angular range includes limiting the incident angle of the X-rays scattered by the scatterer within the predetermined angular range by the grid having a plurality of holes through which X-rays are transmitted.

19. The tomosynthesis imaging method according to claim 18, further comprising storing a calibration image based on X-ray detection data according to X-rays that are transmitted through an ambient gas instead of the object in a memory,
   wherein the step of generating the tomosynthesis image includes calibrating the tomosynthesis image of the object with the stored calibration image to obtain a calibrated tomosynthesis image.

20. The tomosynthesis imaging method according to claim 17, wherein the step of detecting X-rays further comprises detecting the X-rays transmitted through the object together with the incident angle of the X-rays by a detector utilizing Compton scattering,
   the detector comprises:
      a chamber;
      a scattering X-ray detector detecting a detection position and a detection time of scattered X-rays due to Compton scattering of the X-rays that are scattered by the scatterer, transmitted through the object, and enter the chamber; and
      an electron detector detecting a detection position and a detection time of ionized electrons based on recoiling electrons due to the Compton scattering; and
   the method further comprises determining the incident angle of the X-rays based on detection results of the scattering X-ray detector and the electron detector.

* * * * *